United States Patent
Ramsden et al.

(10) Patent No.: US 11,312,689 B2
(45) Date of Patent: Apr. 26, 2022

(54) COMPOUNDS AND THEIR USE FOR THE TREATMENT OF ALPHA1-ANTITRYPSIN DEFICIENCY

(71) Applicant: Z Factor Limited, Babraham (GB)

(72) Inventors: Nigel Ramsden, Babraham (GB); David John Fox, Coventry (GB); James Andrew Huntington, Babraham (GB)

(73) Assignee: Z FACTOR LIMITED, Cambridge (GB)

( * ) Notice: Subject to any disclaimer, the term of this patent is extended or adjusted under 35 U.S.C. 154(b) by 0 days.

(21) Appl. No.: 17/345,928

(22) Filed: Jun. 11, 2021

(65) Prior Publication Data
US 2021/0332015 A1   Oct. 28, 2021

Related U.S. Application Data

(63) Continuation of application No. PCT/GB2019/053552, filed on Dec. 13, 2019.

(30) Foreign Application Priority Data

Dec. 14, 2018 (GB) ...................................... 1820450

(51) Int. Cl.
*C07D 239/36* (2006.01)
*A61P 1/16* (2006.01)
*A61K 9/00* (2006.01)

(52) U.S. Cl.
CPC .......... *C07D 239/36* (2013.01); *A61K 9/0053* (2013.01); *A61P 1/16* (2018.01); *C07B 2200/05* (2013.01)

(58) Field of Classification Search
CPC ....... C07D 239/36; A61P 1/16; A61K 9/0053; C07B 2200/05
USPC ......................................................... 514/269
See application file for complete search history.

(56) References Cited

U.S. PATENT DOCUMENTS

| | | | |
|---|---|---|---|
| 8,436,013 B2 | 5/2013 | Liu et al. | |
| 2010/0076018 A1* | 3/2010 | Liu ..................... | A61K 31/4741 514/311 |
| 2015/0045344 A1 | 2/2015 | Von Nussbaum et al. | |

FOREIGN PATENT DOCUMENTS

| | | |
|---|---|---|
| WO | WO-0152830 A2 | 7/2001 |
| WO | WO-2008143633 A2 | 11/2008 |
| WO | WO-2020120992 A1 | 6/2020 |

OTHER PUBLICATIONS

Bouchecareilh et al. Histone deacetylase inhibitor (HDACi) suberoylanilide hydroxamic acid (SAHA)-mediated correction of α1-antitrypsin deficiency. J Biol Chem 287(45):38265-38278 (2012).
Mallya et al. Small molecules block the polymerization of Z alpha1-antitrypsin and increase the clearance of intracellular aggregates. J Med Chem 50(22):5357-5363 (2007).
PCT/GB2019/053552 International Search Report and Written Opinion dated Mar. 2, 2020.
Berthelier et al. Discovery of an Inhibitor of Z-Alpha1 Antitrypsin Polymerization. PLoS One 10(5):e0126256 (May 11, 2015).
Burrows et al. Chemical chaperones mediate increased secretion of mutant alpha 1-antitrypsin (alpha 1-AT) Z: A potential pharmacological strategy for prevention of liver injury and emphysema in alpha 1-AT deficiency. PNAS USA 97(4):1796-1801 (2000).
Carlson et al. Accumulation of PiZ alpha 1-antitrypsin causes liver damage in transgenic mice. J. Clin Invest 83:1183-90 (1989).
Chang et al. Small-molecule peptides inhibit Z alpha1-antitrypsin polymerization. J. Cell. Mol. Med. 13(8B):2304-2316 (2009).
Dycaico et al. Neonatal hepatitis induced by alpha 1-antitrypsin: a transgenic mouse model. Science 242:1409-12 (1988).
Elkins et al. Variability in high-throughput ion-channel screening data and consequences for cardiac safety assessment. J Pharmacol Toxicol Methods 68:112-122 (2013).
Ellioitt et al. Topography of a 2.0 Å structure of alpha1-antitrypsin reveals targets for rational drug design to prevent conformational disease. Protein Science 9:1274-1281 (2000).
Gould et al. Salt Selection for Basic Drugs. Int J. Pharm. 33:201-217 (1986).
Huntington. How and why the Z variant of $\alpha_1$-antitrypson polymerises, and what can be done about it. 7th International Symposium on Serpin Biology, Structure and Function (Apr. 1, 2014).
Huntington. How and why the Z variant of $\alpha_1$-antitrypson polymerises, and what can be done about it. Xiiith International Symposium on Proteinases, Inhibitors and Biological Control (Sep. 23, 2012).
Knaupp et al. Kinetic instability of the serpin Z alpha1-antitrypsin promotes aggregation. J. Mol. Biol. 396:375-383 (2010).

(Continued)

*Primary Examiner* — Yevgeny Valenrod
(74) *Attorney, Agent, or Firm* — Wilson Sonsini Goodrich & Rosati (57) ABSTRACT

The invention relates to oxopyrimidinyl-methyl-benzamide derivatives, for example in a pharmaceutically acceptable salt form or crystal form, pharmaceutical compositions comprising the derivatives, and their medical use, in particular for use in the treatment of $\alpha_1$-antitrypsin deficiency (A1AD or AATD).

8 Claims, 8 Drawing Sheets

(56) References Cited

OTHER PUBLICATIONS

Parfrey et al. Targeting a surface cavity of alpha 1-antitrypsin to prevent conformational disease. J. Biol. Chem. 278(35):33060-33066 (2003).

Seyama et al. Siiyama (serine 53 (TCC) to phenylalanine 53 (TTC)). A new alpha 1-antitrypsin-deficient variant with mutation on a predicted conserved residue of the serpin backbone. J Biol Chem 266:12627-32 (1991).

Weaver et al. Cytochrome P450 inhibition using recombinant proteins and mass spectrometry/multiple reaction monitoring technology in a cassette incubation. Drug Metab Dispos 31(7):955-966 (2003).

* cited by examiner

COMPOUNDS AND THEIR USE FOR THE TREATMENT OF ALPHA1-ANTITRYPSIN DEFICIENCY

CROSS-REFERENCE

This application is the by-pass continuation of International Application No. PCT/GB2019/053552, filed Dec. 13, 2019, which claims the benefit of GB Application No. 1820450.3, filed Dec. 14, 2018, each of which are incorporated herein by reference in their entireties.

SUMMARY

The invention relates to N,N-dimethyl-4-((6-oxopyrimidin-1(6H)-yl)methyl)benzamide and related compounds, and their medical use.

$\alpha_1$-Antitrypsin (A1AT) is a member of the serpin superfamily produced by the liver and secreted into the blood. It inhibits a variety of serine proteases, especially neutrophil elastase. When blood levels of A1AT are low, excessive neutrophil elastase activity degrades lung tissue resulting in respiratory complications such as chronic obstructive pulmonary disease (COPD).

The reference range of A1AT in blood is 0.9-2.3 g/L. Levels lower than this are typical of $\alpha_1$-antitrypsin deficiency (A1AD or AATD), a genetic disorder caused by mutations in the SERPINA1 gene, coding for A1AT. The Z mutation, the most common cause of AATD, is the substitution of glutamate to lysine at position 366 of A1AT (UniProtKB—P01009 (A1AT_HUMAN)), corresponding to position 342 in the mature protein (Z A1AT). The Z mutation affects the folding of A1AT resulting in only a small fraction acquiring the native/active state. The remainder is either cleared as misfolded protein or accumulates in the liver as stable polymers. As a consequence of the misfolding, homozygous carriers of the Z mutation (ZZ) have plasma levels of A1AT that are 10-15% of normal, predisposing carriers to COPD. Accumulation of Z A1AT polymers in liver cells predisposes carriers to cirrhosis, liver cancer and other liver pathologies.

The current treatment for the lung manifestation of AATD involves augmentation therapy using A1AT concentrates prepared from the plasma of blood donors. The US FDA has approved the use of four A1AT products: Prolastin, Zemaira, Glassia, and Aralast. Dosing is via once weekly intravenous infusion. Augmentation therapy has been demonstrated to slow progression of COPD. The liver manifestations of AATD (e.g. cirrhosis and cancer) are treated with steroids and liver transplantation. Investigational approaches to improved treatment of the liver manifestations include inhibition of Z A1AT polymerisation and increased clearance of polymers through the activation of autophagy. Investigational approaches to improved treatment of both the lung and the liver manifestations are directed towards improvement of Z A1AT folding and secretion.

Elliott et al (Protein Science, 2000, 9, 1274-1281) have described an X-ray crystal structure of A1AT and identified five cavities that are potential targets for rational drug design to develop agents that will affect Z A1AT polymerisation.

Parfrey et al (J. Biol. Chem., 2003, 278, 35, 33060-33066) have further defined a single cavity that is a potential target for rational drug design to develop agents that will affect Z A1AT polymerisation.

Knaupp et al (J. Mol. Biol., 2010, 396, 375-383) have shown that bis-ANS (4,4'-dianilino-1,1'-binaphthyl-5,5'-disulfonate) is able to bind to Z A1AT, but not to wild-type, A1AT (M), with 1:1 stoichiometry and a $K_d$ of 700 nM.

Chang et al (J. Cell. Mol. Med., 2009, 13, 8B, 2304-2316) have reported a series of peptides, including Ac-TTAI-NH$_2$, that inhibit Z A1AT polymerization.

Burrows et al (Proc. Nat. Acad. Sci., 2000, 97, 4, 1796-1801) have shown that a series of non-selective chaperones, including 4-phenylbutyric acid, glycerol and trimethylamine oxide, are able to increase Z A1AT levels in cell supernatants and mouse models.

Bouchecareilh et al (Journal of Biological Chemistry, 2012, 287, 45, 38265-38278) describe the use of histone deacetylase inhibitors, in particular SAHA (suberoylanilide hydroxamic acid) to increase the secretion of both wild-type (M) and Z A1AT from cells.

Berthelier et al (PLOS ONE, May 11, 2015) have demonstrated that S-(4-nitrobenzyl)-6-thioguanosine is able to prevent Z A1AT polymerisation in vitro.

Mallya et al (J. Med. Chem., 2007, 50, 22, 5357-5363) describe a series of phenols, such as N-(4-hydroxy-3,5-dimethylphenyl)-2,5-dimethylthiophene-3-sulfonamide, able to block polymerisation of Z A1AT in vitro.

Huntington (XIIIth International Symposium on Proteinases, Inhibitors and Biological Control, 23 Sep. 2012, and 7$^{th}$ International Symposium on Serpin Biology, Structure and Function, 1 Apr. 2014) discussed a cavity from an X-ray crystal structure of Z A1AT that is a potential target for rational drug design to develop agents that will affect Z A1AT polymerisation.

U.S. Pat. No. 8,436,013B2 discloses a wide variety of structures able to increase secretion of Z A1AT from cells in the micromolar range.

Compounds with CAS registry numbers 1797054-78-4 and 1219580-65-0 are listed in the Aurora Building Blocks catalogue.

According to one aspect of the present invention, there is provided N,N-dimethyl-4-((6-oxopyrimidin-1(6H)-yl)methyl)benzamide:

We have found that N,N-dimethyl-4-((6-oxopyrimidin-1(6H)-yl)methyl)benzamide is shown surprisingly to be highly effective at increasing levels of correctly folded, and hence active, Z A1AT, whilst having no effect on the secretion of wild type (M) A1AT or of the Siiyama variant of A1AT.

According to another aspect of the present invention, there is provided N-methyl-4-((6-oxopyrimidin-1(6H)-yl)methyl)benzamide:

We have found that N,N-dimethyl-4-((6-oxopyrimidin-1(6H)-yl)methyl)benzamide is shown surprisingly to be highly effective at increasing levels of correctly folded, and hence active, Z A1AT, whilst having no effect on the secretion of wild type (M) A1AT or of the Siiyama variant of A1AT.

According to a further aspect of the present invention, there is provided N,N-bis(methyl-d₃)-4-((6-oxopyrimidin-1(6H)-yl)methyl)benzamide:

We have found that N,N-dimethyl-4-((6-oxopyrimidin-1(6H)-yl)methyl)benzamide is shown surprisingly to be highly effective at increasing levels of correctly folded, and hence active, Z A1AT, whilst having no effect on the secretion of wild type (M) A1AT or of the Siiyama variant of A1AT.

The compound of the invention may be in a pharmaceutically acceptable salt form or crystal form.

The term "pharmaceutically acceptable salt" refers to a pharmaceutically acceptable mono organic or inorganic salt of the compound of the invention. This may include addition salts of inorganic acids such as hydrochloride, hydrobromide, hydroiodide, sulphate, phosphate, diphosphate and nitrate or of organic acids such as acetate, maleate, fumarate, tartrate, succinate, citrate, lactate, methanesulphonate, p-toluenesulphonate, palmoate and stearate. Exemplary salts also include oxalate, chloride, bromide, iodide, bisulphate, acid phosphate, isonicotinate, salicylate, acid citrate, oleate, tannate, pantothenate, bitartrate, ascorbate, gentisinate, gluconate, glucuronate, saccharate, formate, benzoate, glutamate, ethanesulfonate, and benzenesulfonate salts. For other examples of pharmaceutically acceptable salts, reference can be made to Gould (1986, Int J Pharm 33: 201-217).

According to a further aspect of the invention, there is provided a pharmaceutical composition comprising the compound of the invention as described herein and a pharmaceutically or therapeutically acceptable excipient or carrier.

The term "pharmaceutically or therapeutically acceptable excipient or carrier" refers to a solid or liquid filler, diluent or encapsulating substance which does not interfere with the effectiveness or the biological activity of the active ingredients and which is not toxic to the host, which may be either humans or animals, to which it is administered. Depending upon the particular route of administration, a variety of pharmaceutically acceptable carriers such as those well known in the art may be used. Non-limiting examples include sugars, starches, cellulose and its derivatives, malt, gelatin, talc, calcium sulfate, vegetable oils, synthetic oils, polyols, alginic acid, phosphate buffered solutions, emulsifiers, isotonic saline, and pyrogen-free water.

All suitable modes of administration are contemplated according to the invention. For example, administration of the medicament may be via oral, subcutaneous, direct intravenous, slow intravenous infusion, continuous intravenous infusion, intravenous or epidural patient controlled analgesia (PCA and PCEA), intramuscular, intrathecal, epidural, intracisternal, intraperitoneal, transdermal, topical, transmucosal, buccal, sublingual, transmucosal, inhalation, intranasal, intra-atricular, intranasal, rectal or ocular routes. The medicament may be formulated in discrete dosage units and can be prepared by any of the methods well known in the art of pharmacy.

All suitable pharmaceutical dosage forms are contemplated. Administration of the medicament may for example be in the form of oral solutions and suspensions, tablets, capsules, lozenges, effervescent tablets, transmucosal films, suppositories, buccal products, oral mucoretentive products, topical creams, ointments, gels, films and patches, transdermal patches, abuse deterrent and abuse resistant formulations, sterile solutions suspensions and depots for parenteral use, and the like, administered as immediate release, sustained release, delayed release, controlled release, extended release and the like.

Another aspect of the invention is the use of the compound of the invention as defined herein in the manufacture of a medicament for the treatment of a disease or disorder.

A further aspect of the invention is the compound of the invention for use as an inducer of Z A1AT secretion.

Further provided is the compound of the invention as defined herein for use in the treatment of a disease or disorder.

The invention also encompasses a method of treating a disease or disorder, comprising the step of administering the compound or the pharmaceutical composition of the invention as defined herein to a patient in need of same.

The invention further encompasses the use of a compound of the invention as an inducer of Z A1AT secretion. The use may be in the treatment of a disease or disorder. Additionally or alternatively, the use may be in vitro, for example in an in vitro assay.

A disease or disorder suitable for treatment according to the relevant aspects of the invention is one which is characterised by low plasma levels of A1AT, for example AATD.

The use of a numerical range in this description is intended unambiguously to include within the scope of the invention all individual integers within the range and all the combinations of upper and lower limit numbers within the broadest scope of the given range.

As used herein, the term "comprising" is to be read as meaning both comprising and consisting of Consequently, where the invention relates to a "pharmaceutical composition comprising as active ingredient" a compound, this terminology is intended to cover both compositions in which other active ingredients may be present and also compositions which consist only of one active ingredient as defined.

Unless otherwise defined, all the technical and scientific terms used here have the same meaning as that usually understood by an ordinary specialist in the field to which this invention belongs. Similarly, all the publications, patent applications, all the patents and all other references mentioned here are incorporated by way of reference in their entirety (where legally permissible).

Particular non-limiting examples of the present invention will now be described with reference to the following drawings, in which:

FIG. 4 is a graph showing the effect of N,N-dimethyl-4-((6-oxopyrimidin-1(6H)-yl)methyl)benzamide on Z A1AT levels in mice expressing human Z A1AT (huZ mice). Mice were treated with vehicle, 5, 15 and 50 mg/kg N,N-dimethyl-4-((6-oxopyrimidin-1(6H)-yl)methyl)benzamide twice a day by oral gavage for 14 consecutive days. Blood was taken on days −12, −7 and −5 and plasma prepared to determine circulating basal levels of human Z A1AT. Plasma samples collected on the last three days of the study (days 12, 13 and 14) were used to determine the effect of N,N-dimethyl-4-((6-oxopyrimidin-1(6H)-yl)methyl)benzamide treatment on circulating human Z A1AT levels compared to basal levels. The x-axis is the treatment dose of N,N-dimethyl-4-((6-oxopyrimidin-1(6H)-yl)methyl)benzamide in mg/kg; the y-axis is the mean percentage level of human Z A1AT compared to baseline levels for each treatment group;

EXPERIMENTAL

Example 1

N,N-dimethyl-4-((6-oxopyrimidin-1(6H)-yl)methyl) benzamide

N,N-dimethyl-4-((6-oxopyrimidin-1(6H)-yl)methyl)benzamide was prepared using the following sequential synthesis procedures.

(a) Synthesis of tert-butyl 4-((6-oxopyrimidin-1 (6H)-yl)methyl)benzoate

Pyrimidin-4(3H)-one (5 g, 32 mmol) and caesium carbonate (50.85 g, 156 mmol) were stirred in dimethylformamide (50 ml) for 10 minutes at room temperature. Tert-butyl 4-(bromomethyl)benzoate (14.11 g, 52 mmol) was added and the reaction was stirred for 3 hours. The reaction was diluted with water and the resulting yellow precipitate collected by filtration. The crude product was purified by column chromatography on silica, eluting with ethyl acetate/hexane (30% to 33%) to give tert-butyl 4-((6-oxopyrimidin-1(6H)-yl)methyl)benzoate. Tlc Rf 0.2 1:1 Ethyl acetate/hexane.

(b) Synthesis of 4-((6-oxopyrimidin-1(6H)-yl) methyl)benzoic acid

Tert-butyl 4-((6-oxopyrimidin-1(6H)-yl)methyl)benzoate (10 g, 35 mmol) was dissolved in dichloromethane (50 ml) and trifluoroacetic acid (70 ml) was added slowly. The reaction was stirred for 3 hours at room temperature. The reaction was concentrated under reduced pressure and the resulting oil stirred with diethyl ether (300 ml) for 20 minutes at room temperature. The resultant solid was collected by filtration, washed with diethyl ether (2×30 ml) and dried in vacuo to give 4-((6-oxopyrimidin-1(6H)-yl)methyl)benzoic acid.

(c) Synthesis of N,N-dimethyl-4-((6-oxopyrimidin-1(6H)-yl)methyl)benzamide

4-((6-oxopyrimidin-1(6H)-yl)methyl)benzoic acid (16 g, 69 mmol) and N-(3-dimethylaminopropyl)-N'-ethylcarbodiimide hydrochloride (18 g, 139 mmol) were stirred in tetrahydrofuran (100 ml) for 10 minutes at 0° C. under nitrogen. The reaction was then allowed to warm to room temperature. Triethylamine (21.11 g, 208 mmol) and dimethylamine (2M solution in tetrahydrofuran, 69 mmol) were added and the reaction was stirred for 2 hours. The reaction was concentrated under reduced pressure and the residue columned on silica eluting with 4% methanol in dichloromethane. Product containing fractions were concentrated to give N,N-dimethyl-4-((6-oxopyrimidin-1(6H)-yl)methyl)benzamide.

Tlc Rf 0.8 10% methanol in dichloromethane.

m/z: 257.96 (calc 258.12)

$^1$H NMR (400 MHz, d6 DMSO) δ 8.69 (1H, s), 7.94 (1H, d), 7.38 (4H, m), 6.44 (1H, d), 5.13 (2H, s), 2.96 (3H, br s), 2.87 (3H, br s).

N,N-dimethyl-4-((6-oxopyrimidin-1(6H)-yl)methyl)benzamide could also be prepared by alkylation of pyrimidin-4(3H)-one with 4-(bromomethyl)-N,N-dimethylbenzamide in a similar manner to step a).

Example 2

N-methyl-4-((6-oxopyrimidin-1(6H)-yl)methyl)benzamide

N-methyl-4-((6-oxopyrimidin-1(6H)-yl)methyl)benzamide was prepared similarly to N,N-dimethyl-4-((6-oxopyrimidin-1(6H)-yl)methyl)benzamide using methylamine instead of dimethylamine in step c.

m/z: 242.90 (calc 243.10)

1H NMR (400 MHz, d6 DMSO) δ 8.69 (1H, s), 8.42 (1H, br m), 7.94 (1H, d), 7.79 (2H, d), 7.37 (2H, d), 6.43 (1H, d), 5.13 (2H, s), 2.77 (3H, s).

Example 3

N,N-(bis-methyl-d$_3$)-4-((6-oxopyrimidin-1(6H)-yl)methyl)benzamide

N,N-(bis-methyl-d$_3$)-4-((6-oxopyrimidin-1(6H)-yl)methyl)benzamide was prepared similarly to N,N-dimethyl- 4-((6-oxopyrimidin-1(6H)-yl)methyl)benzamide using $d_6$-dimethylamine instead of dimethylamine in step c.

Tlc Rf 0.8 10% methanol in dichloromethane.

$^1$H NMR (400 MHz, d6 DMSO) δ 8.69 (1H, s), 7.94 (1H, d), 7.38 (4H, m), 6.44 (1H, d), 5.13 (2H, s).

Example 4

Activity of Compounds of the Invention in an A1AT Cell Secretion Assay Using HEK-Z Cells Methods HEK-Z cells, a human embryonic kidney cell line stably transfected with the human Z A1AT gene, were plated into 96 well plates ($3.0 \times 10^5$ cells/ml with 200 μl of media/well) overnight at 37° C. in a humidified atmosphere containing 5% $CO_2$. Following incubation cells were washed with 200 μl serum-free media three times and media was replaced with treatments in quadruplicate using serum-free media containing either vehicle, 10 μM suberanilohydroxamic acid (SAHA), N,N-dimethyl-4-((6-oxopyrimidin-1(6H)-yl)methyl)benzamide (at concentrations of 10, 33, 100 and 333 nM), N,N-(bis-methyl-d3)-4-((6-oxopyrimidin-1(6H)-yl)methyl)benzamide (at concentrations of 10, 33, 100 and 333 nM) or N-methyl-4-((6-oxopyrimidin-1(6H)-yl)methyl)benzamide (at concentrations of 10, 33, 100 and 333 nM) for 48 h in a 37° C. incubator in a final volume of 200 μl. At the end of the incubation step the supernatants were removed from the wells, centrifuged at 1000×g at 4° C. for 10 min and were assayed for human A1AT levels by ELISA (Human Serpin A1/$α_1$-antitrypsin duo set ELISA, R& D Systems, DY1268) per manufacturer's instructions.

Briefly, a 96 well plate was coated with human A1AT capture antibody overnight at room temperature (1:180 dilution from stock, 100 μl final volume/well). The capture antibody was then removed and wells washed three times with 300 μl wash buffer (0.05% Tween 20 in PBS) and then 200 μl reagent diluent (25% Tween 20 in PBS) was incubated in each well for 1 h at room temperature. Diluted samples, standards (125, 250, 500, 1000, 2000, 4000 and 8000 pg/ml A1AT) or blanks were then added to each well in duplicate and the plates were covered with a plate sealer and left at room temperature for 2 h. At the end of the sample incubation step, samples were removed and all wells washed as previously and 100 μl detection antibody (1:180 dilution from stock) was added to each well and incubated for a further 2 h at room temperature. Following incubation with detection antibody, supernatant was removed and wells were washed as previously and 100 μl streptavidin-HRP solution (1:200 dilution from stock) was added to each well for 20 min in the dark. After which, 50 μl stop solution (2M $H_2SO_4$) was added and optical density (OD) of each well was read at 450 nm with 570 nm blank subtracted from each well using a microplate reader. A 4 parameter logistic curve was constructed using GraphPad Prism 7 and A1AT concentrations were determined in each sample by interpolation from a standard curve and multiplying by the appropriate dilution factor.

Results

The amount of A1AT secreted from transfected HEK-EBNA cells into the media was measured by ELISA. SAHA at 10 μM was used a positive control for all in vitro A1AT secretion experiments.

Figure 1:
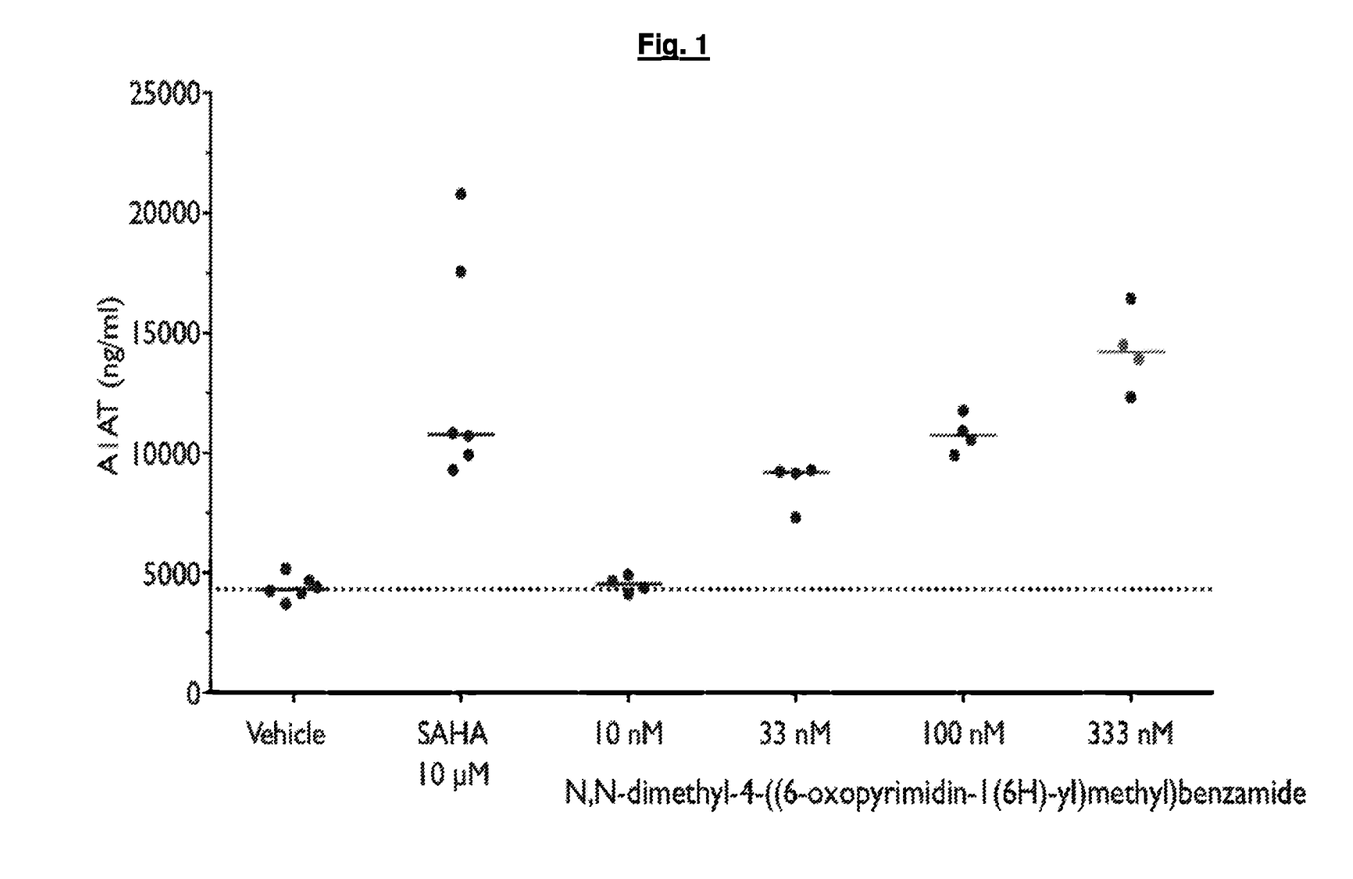
FIG. 1 is a graph showing the dose dependent effect of N,N-dimethyl-4-((6-oxopyrimidin-1(6H)-yl)methyl)benzamide in an in vitro A1AT cell secretion assay using HEK-EBNA cells containing the Z A1AT plasmid. Vehicle and 10 μM SAHA were tested on each plate as controls. The x-axis shows various treatments of the cells: vehicle, SAHA and increasing concentrations of N,N-dimethyl-4-((6-oxopyrimidin-1(6H)-yl)methyl)benzamide, the y-axis is the concentration of A1AT in the cell supernatant (in ng/ml)

The data in FIG. 1 show that N,N-dimethyl-4-((6-oxopyrimidin-1(6H)-yl)methyl)benzamide stimulates secretion of Z A1AT in a dose dependent manner as measured by ELISA.

Figure 5:
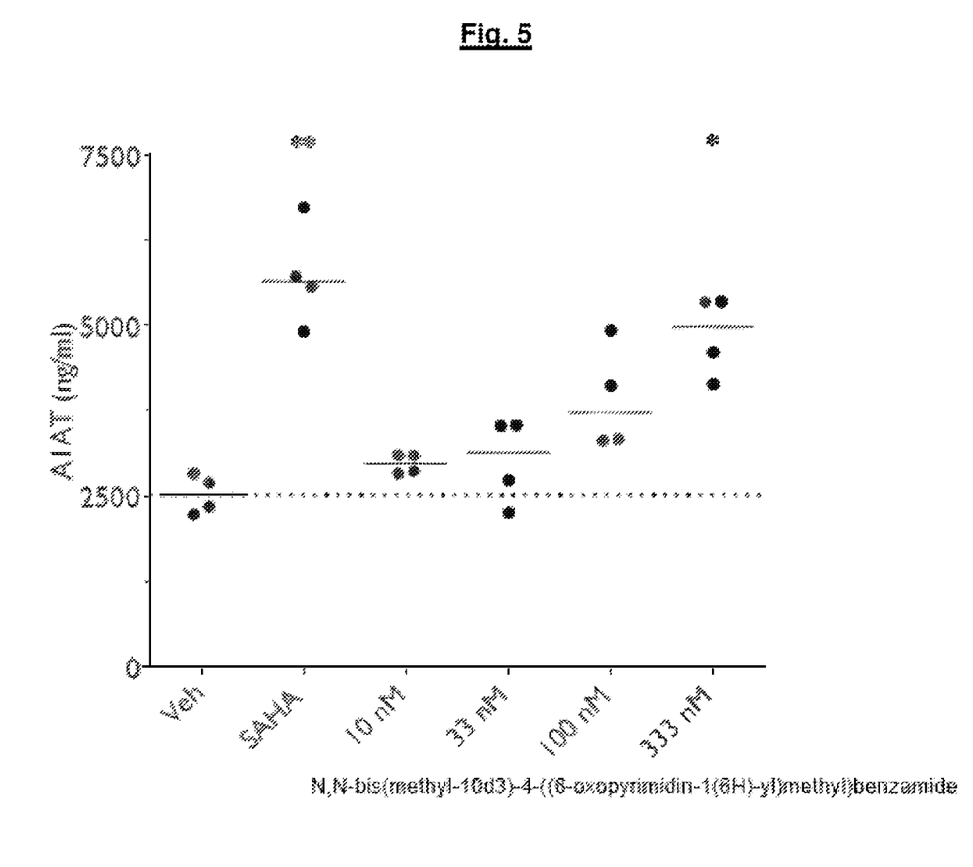
FIG. 5 is a graph showing the dose dependent effect of N,N-(bis-methyl-$d_3$)-4-((6-oxopyrimidin-1(6H)-yl)methyl) benzamide in an in vitro A1AT cell secretion assay using HEK-EBNA cells containing the Z A1AT plasmid. Vehicle and 10 μM SAHA were tested on each plate as controls. The x-axis shows various treatments of the cells: vehicle, SAHA and increasing concentrations of N,N-(bis-methyl-$d_3$)-4-((6-oxopyrimidin-1(6H)-yl)methyl)benzamide, the y-axis is the concentration of A1AT in the cell supernatant (in ng/ml)

The data in FIG. 5 show that N,N-(bis-methyl-$d_3$)-4-((6-oxopyrimidin-1(6H)-yl)methyl)benzamide stimulates secretion of Z A1AT in a dose dependent manner as measured by ELISA.

Figure 6:
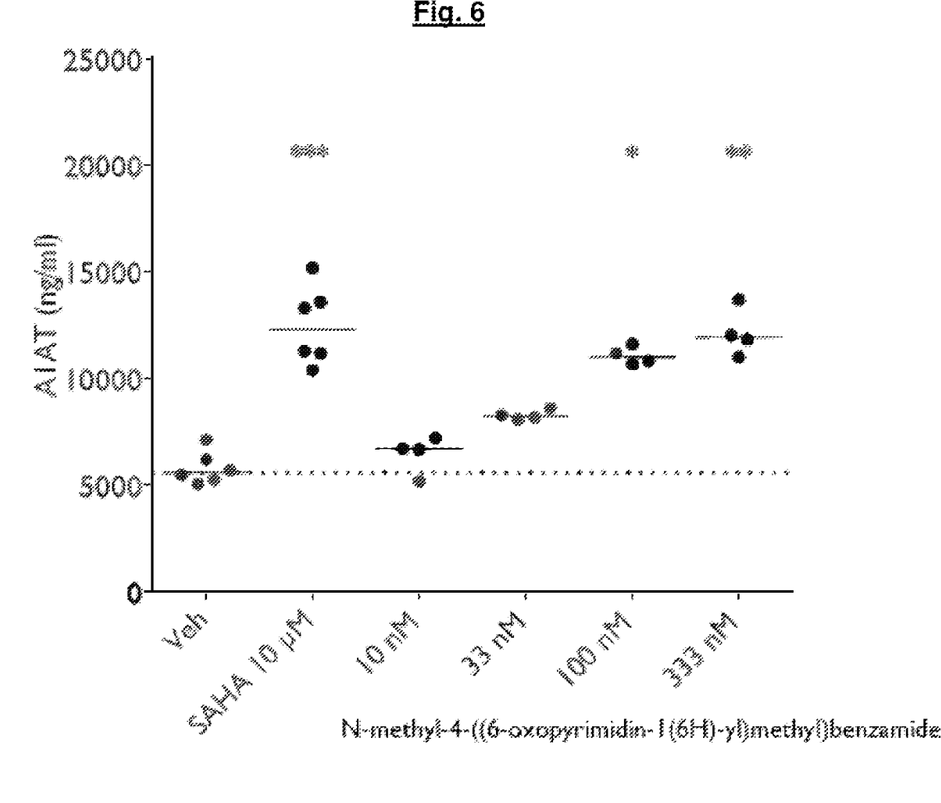
FIG. 6 is a graph showing the dose dependent effect of N-methyl-4-((6-oxopyrimidin-1(6H)-yl)methyl)benzamide in an in vitro A1AT cell secretion assay using HEK-EBNA cells containing the Z A1AT plasmid. Vehicle and 10 μM SAHA were tested on each plate as controls. The x-axis shows various treatments of the cells: vehicle, SAHA and increasing concentrations of N-methyl-4-((6-oxopyrimidin-1(6H)-yl)methyl)benzamide, the y-axis is the concentration of A1AT in the cell supernatant (in ng/ml)

The data in FIG. 6 show that N-methyl-4-((6-oxopyrimidin-1(6H)-yl)methyl)benzamide stimulates secretion of Z A1AT in a dose dependent manner as measured by ELISA.

Example 5

Activity of Compounds of the Invention in an A1AT Cell Secretion Assay Using HEK-M Cells Methods HEK-M cells, a human embryonic kidney cell line stably transfected with the human M A1AT gene, were plated into 96 well plates ($3.0 \times 10^5$ cells/ml with 200 μl of media/well) overnight at 37° C. in a humidified atmosphere containing 5% $CO_2$. Following incubation cells were washed with 200 μl serum-free media three times and media was replaced with serum-free media containing either vehicle, 10 μM suberanilohydroxamic acid (SAHA) or a compound of the invention (at 10 μM) in replicates of six for 48 h in a 37° C. incubator in a final volume of 200 μl. At the end of the incubation step the supernatants were removed from the wells, centrifuged at 1000×g at 4° C. for 10 min and were assayed for human A1AT levels by ELISA (Human Serpin A1/$α_1$-antitrypsin duo set ELISA, R& D Systems, DY1268) per manufacturer's instructions.

Briefly, a 96 well plate was coated with human A1AT capture antibody overnight at room temperature (1:180 dilution from stock, 100 μl final volume/well). The capture antibody was then removed and wells washed three times with 300 μl wash buffer (0.05% Tween 20 in PBS) and then 200 μl reagent diluent (25% Tween 20 in PBS) was incubated in each well for 1 h at room temperature. Diluted samples, standards (125, 250, 500, 1000, 2000, 4000 and 8000 pg/ml A1AT) or blanks were then added to each well in duplicate and the plates were covered with a plate sealer and left at room temperature for 2 h. At the end of the sample incubation step, samples were removed and all wells washed as previously and 100 μl detection antibody (1:180 dilution from stock) was added to each well and incubated for a further 2 h at room temperature. Following incubation with detection antibody, supernatant was removed and wells were washed as previously and 100 μl streptavidin-HRP solution (1:200 dilution from stock) was added to each well for 20 min in the dark. After which, 50 μl stop solution (2M $H_2SO_4$) was added and optical density (OD) of each well was read at 450 nm with 570 nm blank subtracted from each well using a microplate reader. A 4 parameter logistic curve was constructed using GraphPad Prism 7 and A1AT concentrations were determined in each sample by interpolation from a standard curve and multiplying by the appropriate dilution factor.

Results

The amount of A1AT secreted from transfected HEK-EBNA cells into the media was measured by ELISA. SAHA at 10 μM was used a positive control for all in vitro A1AT secretion experiments.

Figure 2:
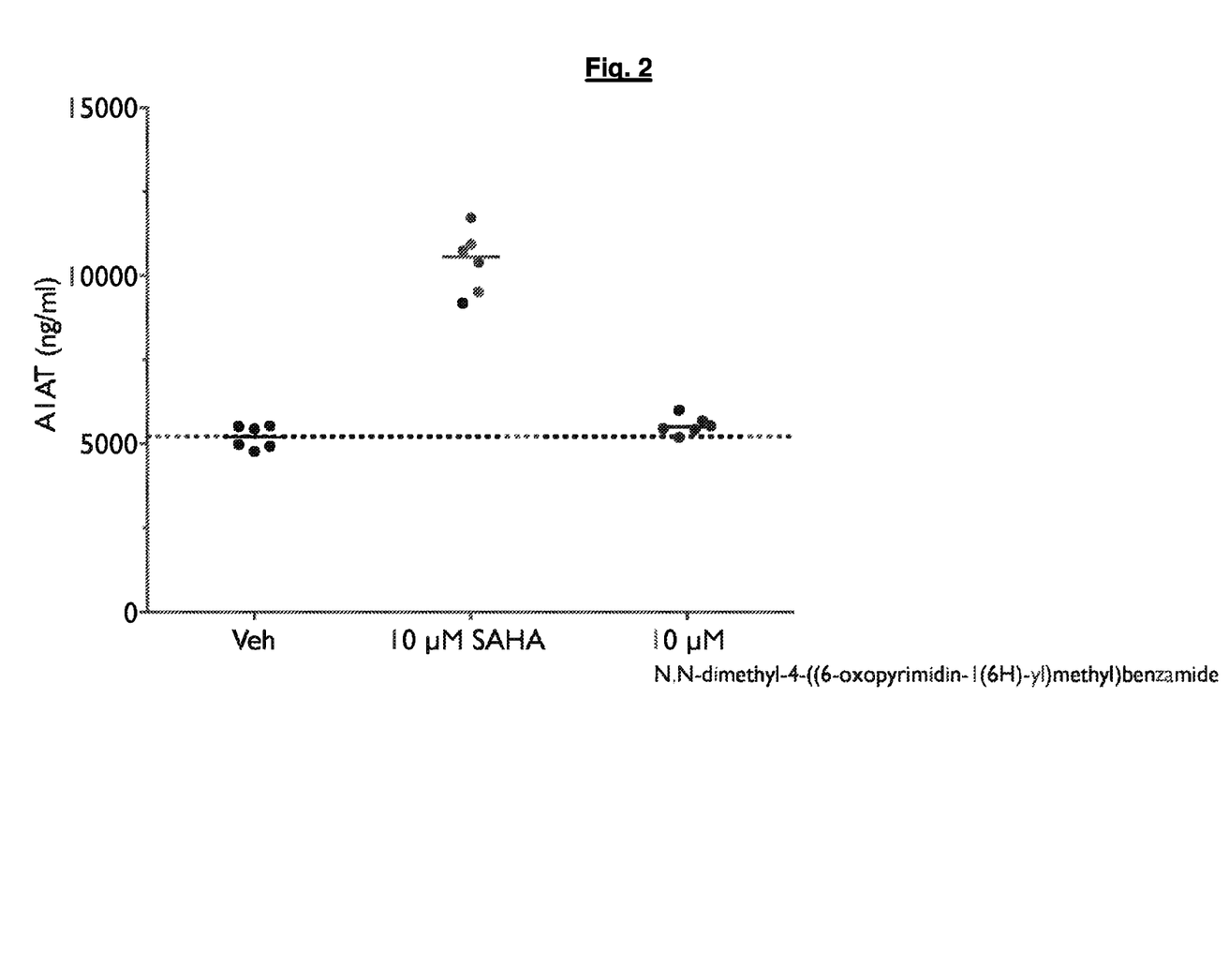
FIG. 2 is a graph showing the effect of N,N-dimethyl-4-((6-oxopyrimidin-1(6H)-yl)methyl)benzamide at 10 μM in an in vitro A1AT cell secretion assay using HEK-EBNA cells containing the M A1AT plasmid. Vehicle and 10 μM SAHA were tested as controls. The x-axis shows various treatments of the cells: vehicle, SAHA and N,N-dimethyl-4-((6-oxopyrimidin-1(6H)-yl)methyl)benzamide, the y-axis is the concentration of A1AT in the cell supernatant (in ng/ml)

The data in FIG. 2 show that N,N-dimethyl-4-((6-oxopyrimidin-1(6H)-yl)methyl)benzamide does not stimulate secretion of M A1AT at 10 μM, as measured by ELISA. In contrast, the positive control 10 μM SAHA stimulates an increase in M A1AT secretion.

Example 6

Activity of Compounds of the Invention in an A1AT Cell Secretion Assay Using HEK-Siiyama Cells The rare Siiyama mutation (Ser 53 to Phe, mature A1AT numbering) was identified in a Japanese male with AATD (Seyama et al J Biol Chem (1991) 266:12627-32). Ser53 is one of the conserved serpin residues and is thought to be important for the organization of the internal core of the A1AT molecule. The change from an uncharged polar to a large nonpolar amino acid on the conserved backbone of the protein affects the folding and intracellular processing of Siiyama A1AT.

Methods

HEK-Siiyama cells, a human embryonic kidney cell line stably transfected with the human Siiyama A1AT gene, were plated into 96 well plates ($3.0 \times 10^5$ cells/ml with 200 µl of media/well) overnight at 37° C. in a humidified atmosphere containing 5% $CO_2$. Following incubation cells were washed with 200 µl serum-free media three times and media was replaced with serum-free media containing either vehicle, 10 µM suberanilohydroxamic acid (SAHA) or a compound of the invention (at 1 or 10 µM) in replicates of eight for 48 h in a 37° C. incubator in a final volume of 200 µl. At the end of the incubation step the supernatants were removed from the wells, centrifuged at 1000×g at 4° C. for 10 min and were assayed for human A1AT levels by ELISA (Human Serpin A1/$\alpha_1$-antitrypsin duo set ELISA, R& D Systems, DY1268) per manufacturer's instructions.

Briefly, a 96 well plate was coated with human A1AT capture antibody overnight at room temperature (1:180 dilution from stock, 100 µl final volume/well). The capture antibody was then removed and wells washed three times with 300 µl wash buffer (0.05% Tween 20 in PBS) and then 200 µl reagent diluent (25% Tween 20 in PBS) was incubated in each well for 1 h at room temperature. Diluted samples, standards (125, 250, 500, 1000, 2000, 4000 and 8000 pg/ml A1AT) or blanks were then added to each well in duplicate and the plates were covered with a plate sealer and left at room temperature for 2 h. At the end of the sample incubation step, samples were removed and all wells washed as previously and 100 µl detection antibody (1:180 dilution from stock) was added to each well and incubated for a further 2 h at room temperature. Following incubation with detection antibody, supernatant was removed and wells were washed as previously and 100 µl streptavidin-HRP solution (1:200 dilution from stock) was added to each well for to 20 min in the dark. After which, 50 µl stop solution (2M $H_2SO_4$) was added and optical density (OD) of each well was read at 450 nm with 570 nm blank subtracted from each well using a microplate reader. A 4 parameter logistic curve was constructed using GraphPad Prism 7 and A1AT concentrations were determined in each sample by interpolation from a standard curve and multiplying by the appropriate dilution factor.

Results

The amount of human A1AT secreted from transfected HEK-EBNA cells into the media was measured by ELISA. SAHA at 10 µM was used a positive control for all in vitro A1AT secretion experiments.

Figure 3:
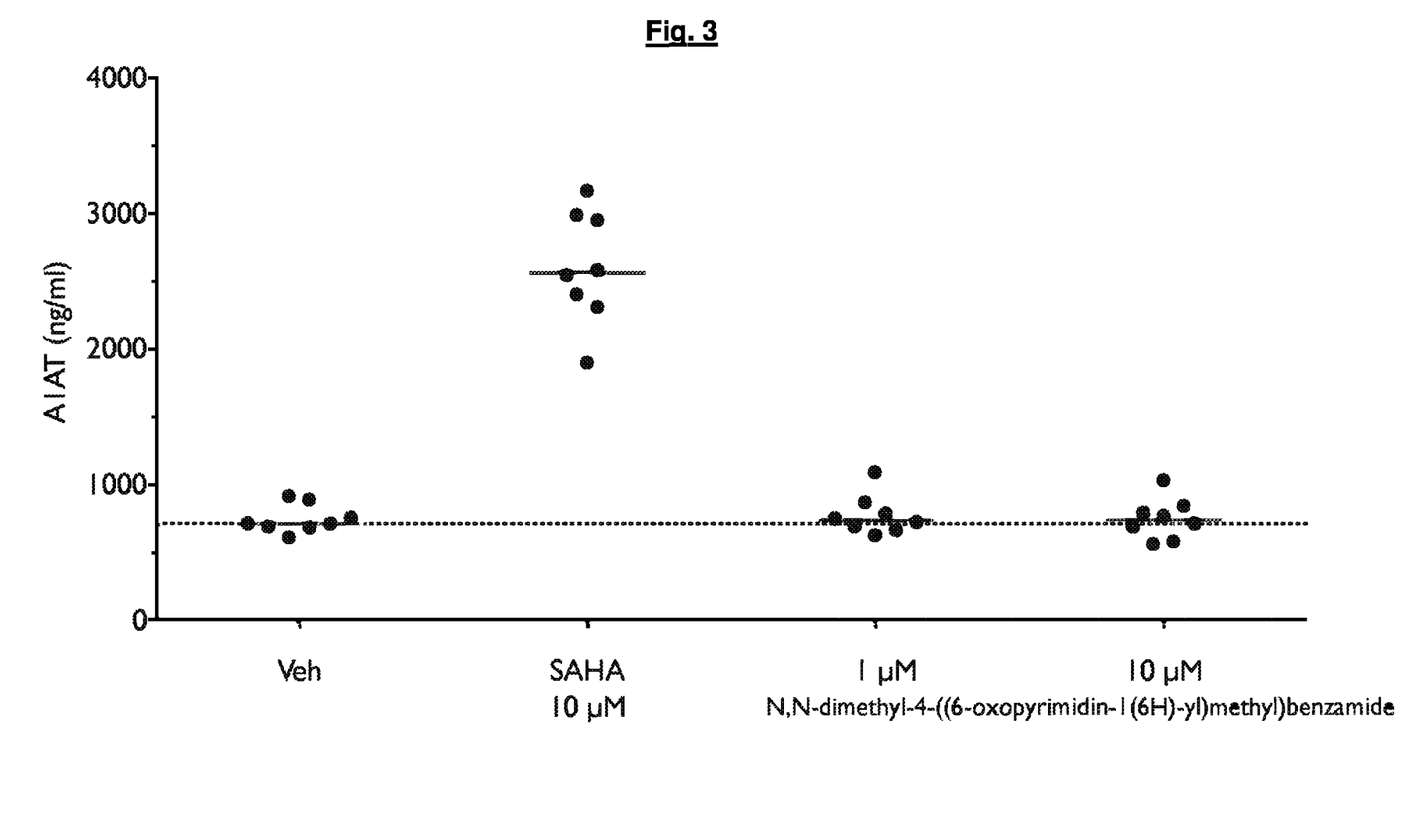
FIG. 3 is a graph showing the effect of N,N-dimethyl-4-((6-oxopyrimidin-1(6H)-yl)methyl)benzamide at 1 and 10 μM in an in vitro A1AT cell secretion assay using HEK-EBNA cells containing the Siiyama A1AT plasmid. Vehicle and 10 μM SAHA were tested as controls. The x-axis shows various treatments of the cells: vehicle, SAHA and two concentrations of N,N-dimethyl-4-((6-oxopyrimidin-1(6H)-yl)methyl)benzamide, the y-axis is the concentration of A1AT in the cell supernatant (in ng/ml)

The data in FIG. 3 show that N,N-dimethyl-4-((6-oxopyrimidin-1(6H)-yl)methyl)benzamide does not stimulate secretion of Siiyama A1AT at 1 or 10 µM, as measured by ELISA. In contrast, the positive control 10 µM SAHA stimulates an increase in Siiyama A1AT secretion.

Example 7

Activity of N,N-dimethyl-4-((6-oxopyrimidin-1(6H)-yl)methyl)benzamide in huZ Mice The huZ mouse (also referred to as the PiZZ mouse) is a transgenic mouse strain that contains multiple copies of the Z variant of the human A1AT gene, developed by two separate groups Dycaico et al (Science (1988) 242:1409-12) and Carlson et al (J. Clin Invest (1989) 83:1183-90). PiZZ mice are on a C57B1/6 background and express the human Z A1AT protein in liver tissue. The mice used in this study are from the progeny of Carlson and colleagues (transgenic line Z11.03). HuZ mice have been used as a tool to assess the effects of compounds on either increasing the circulating levels of Z A1AT in plasma or the effects of compounds on the accumulation of Z A1AT polymers in the liver and associated liver pathology.

Methods

HuZ mice (n=4/group; male or female) with basal human A1AT plasma levels of between 200-600 µg/ml were treated with either vehicle or N,N-dimethyl-4-((6-oxopyrimidin-1(6H)-yl)methyl)benzamide at 5, 15 or 50 mg/kg twice a day by oral gavage for 14 consecutive days. Mice had access to food (standard mouse chow, SAFE diets) and water ad libitum. On study day 14, each mouse was dosed one hour prior to terminal procedures. Blood was taken from each mouse from the tail vein on pre-dosing days −12, −7 and −5 and on dosing days 12, 13 and 14. Blood was collected into microvettes containing EDTA and plasma was prepared by centrifugation at 2700×g at 4° C. for 10 min. Plasma was aliquoted and stored at −80° C. for bioanalysis. Plasma samples from pre-dosing days −12, −7 and −5 were used to determine mean basal levels of human Z A1AT for each mouse. Plasma samples collected the last three dosing days of the study (days 12, 13 and 14) were used to determine the effect of N,N-dimethyl-4-((6-oxopyrimidin-1(6H)-yl) methyl)benzamide on Z A1AT secretion by measuring human Z A1AT levels and comparing to basal levels for each mouse. Human Z A1AT levels in mouse plasma samples were measured by ELISA (Human Serpin A1/$\alpha_1$-antitrypsin duo set ELISA, R& D Systems, DY1268) per manufacturer's instructions.

Briefly, a 96 well plate was coated with human A1AT capture antibody overnight at room temperature (1:180 dilution from stock, 100 µl final volume/well). The capture antibody was then removed and wells washed three times with 300 µl wash buffer (0.05% Tween 20 in PBS) and then 200 µl reagent diluent (25% Tween 20 in PBS) was incubated in each well for 1 h at room temperature. Diluted samples, standards (125, 250, 500, 1000, 2000, 4000 and 8000 pg/ml A1AT) or blanks were then added to each well in duplicate and the plates were covered with a plate sealer and left at room temperature for 2 h. At the end of the sample incubation step, samples were removed and all wells washed as previously and 100 µl detection antibody (1:180 dilution from stock) was added to each well and incubated for a further 2 h at room temperature. Following incubation with detection antibody, supernatant was removed and wells were washed as previously and 100 µl streptavidin-HRP solution (1:200 dilution from stock) was added to each well for 20 min in the dark. After which, 50 µl stop solution (2M $H_2SO_4$) was added and optical density (OD) of each well was read at 450 nm with 570 nm blank subtracted from each well using a microplate reader. A 4 parameter logistic curve was constructed using GraphPad Prism 7 and A1AT concentrations were determined in each sample by interpolation from a standard curve and multiplying by the appropriate dilution factor.

Results

The effect of N,N-dimethyl-4-((6-oxopyrimidin-1(6H)-yl)methyl)benzamide on circulating levels of human Z A1AT was assessed in a huZ mouse model. Mice were treated for 14 consecutive days by oral gavage twice daily at 5, 15 or 50 mg/kg.

Figure 4:
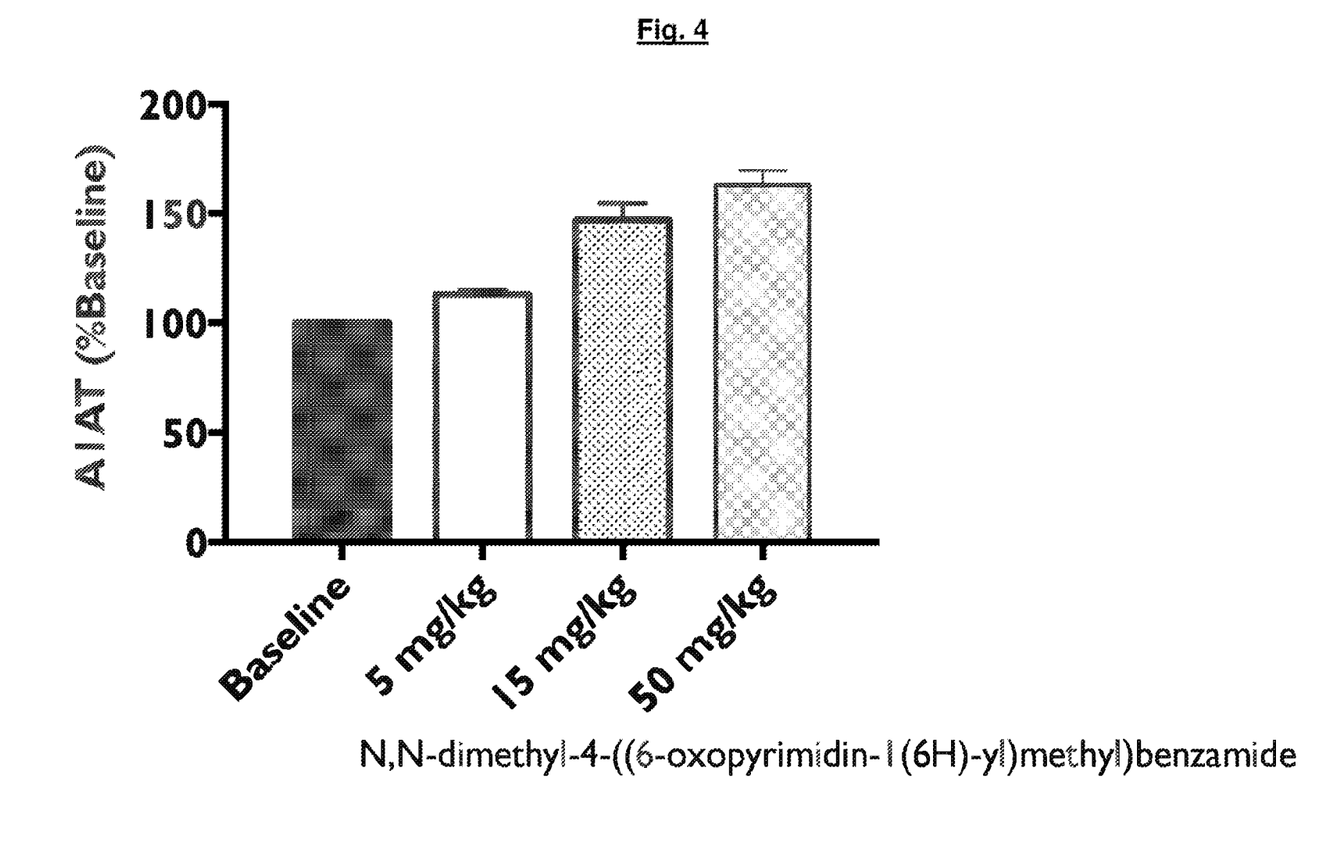

The data in FIG. 4 show that N,N-dimethyl-4-((6-oxopyrimidin-1(6H)-yl)methyl)benzamide stimulates secretion of human Z A1AT compared to baseline levels in huZ mice in a dose dependent manner.

Example 8

Pharmacokinetics of N,N-dimethyl-4-((6-oxopyrimidin-1(6H)-yl)methyl)benzamide in Mice N,N-dimethyl-4-((6-oxopyrimidin-1(6H)-yl)methyl)benzamide was administered to male C57Bl/6 mice intravenously (2 mg/kg) or orally (10 mg/kg) by gavage. Whole blood diluted with water was prepared from these dosed animals over a time course up to 24 hours post dose to allow blood concentrations of drug to be measured by UPLC-MS/MS. The measured drug levels allowed calculation of the following parameters for N,N-dimethyl-4-((6-oxopyrimidin-1(6H)-yl)methyl)benzamide:

Half-life in blood ($t_{1/2}$)=1.9 h
Observed clearance=7.8 ml/min/kg
Volume of distribution (Vz)=1.3 l/kg
Oral $C_{max}$=9311 ng/ml
$AUC_{all}$=15551 ng.h/ml
$AUC_{INF}$=15564 ng.h/ml
Oral Bioavailability (F, $AUC_{INF}$)=73%

Example 9

Pharmacokinetics of Compounds of the Invention in Rats

Compounds were administered to Sprague Dawley rats intravenously (2 mg/kg) or orally (10 mg/kg) by gavage. Whole blood diluted with water was prepared from these dosed animals over a time course up to 24 hours post dose to allow blood concentrations of drug to be measured by UPLC-MS/MS.

The measured compound levels after the administration of N,N-dimethyl-4-((6-oxopyrimidin-1(6H)-yl)methyl)benzamide allowed calculation of the following parameters for N,N-dimethyl-4-((6-oxopyrimidin-1(6H)-yl)methyl)benzamide:

Half-life in blood ($t_{1/2}$)=55 min
Observed clearance=10.6 ml/min/kg
Volume of distribution (Vz)=0.84 l/kg
Oral $C_{max}$=5326 ng/ml
Oral $AUC_{INF}$=16465 ng.h/ml
Oral Bioavailability (F)=104%.

The plasma levels of N-methyl-4-((6-oxopyrimidin-1(6H)-yl)methyl)benzamide at various time points after a 10 mg/Kg oral dose of N,N-dimethyl-4-((6-oxopyrimidin-1(6H)-yl)methyl)benzamide were as shown in Table 1.

TABLE 1

Plasma levels of N-methyl-4-((6-oxopyrimidin-1(6H)-yl)methyl)benzamide after oral dose of N,N-dimethyl-4-((6-oxopyrimidin-1(6H)-yl)methyl)benzamide

| Time (min) | Mean Plasma Level of N-methyl-4-((6-oxopyrimidin-1(6H)-yl)methyl)benzamide (ng/ml) |
| --- | --- |
| 5 | 369 |
| 15 | 548 |
| 30 | 1047 |
| 60 | 1395 |
| 120 | 1465 |
| 240 | 528 |
| 480 | 224 |
| 1440 | 62 |

The plasma levels of N-methyl-4-((6-oxopyrimidin-1(6H)-yl)methyl)benzamide at various time points after a 2 mg/Kg iv dose of N,N-dimethyl-4-((6-oxopyrimidin-1(6H)-yl)methyl)benzamide were as shown in Table 2.

TABLE 2

Plasma levels of N-methyl-4-((6-oxopyrimidin-1(6H)-yl)methyl)benzamide after iv dose of N,N-dimethyl-4-((6-oxopyrimidin-1(6H)-yl)methyl)benzamide

| Time (min) | Mean Plasma Level of N-methyl-4-((6-oxopyrimidin-1(6H)-yl)methyl)benzamide (ng/ml) |
| --- | --- |
| 2 | 51 |
| 6 | 78 |
| 10 | 115 |
| 15 | 102 |
| 30 | 257 |
| 60 | 321 |
| 240 | 90 |
| 480 | 13 |

The measured compound levels after the administration of N-methyl-4-((6-oxopyrimidin-1(6H)-yl)methyl)benzamide allowed calculation of the following parameters for N-methyl-4-((6-oxopyrimidin-1(6H)-yl)methyl)benzamide:

Half-life in blood ($t_{1/2}$)=63 min
Observed clearance=10.6 ml/min/kg
Volume of distribution (Vz)=1.0 l/kg.

The measured compound levels after the administration of N,N-bis(methyl-d3)-4-((6-oxopyrimidin-1(6H)-yl)methyl)benzamide allowed calculation of the following parameters for N,N-bis(methyl-$d_3$)-4-((6-oxopyrimidin-1(6H)-yl)methyl)benzamide:

Half-life in blood ($t_{1/2}$)=52 min
Observed clearance=10.6 ml/min/kg
Volume of distribution (Vz)=0.72 l/kg.

Example 10

Mouse, Rat and Human Hepatocyte Stability of the Compounds of the Invention

The intrinsic clearances ($CL_{int}$) and half-lives of the compounds of the invention were measured in a hepatocyte suspension of cryopreserved male C57BL6 mouse hepatocytes, a hepatocyte suspension of cryopreserved rat hepatocytes or a mixed hepatocyte suspension of cryopreserved human hepatocytes. Briefly, the compound was incubated with hepatocyte suspensions at 37° C. over a time course and the remaining compound at each time point was assessed by mass spectrometry (UPLC-MS/MS). $CL_{int}$ in mouse, rat and human hepatocytes was <3 µl/min/$10^6$ cells for all compounds. Half-life in mouse, rat and human hepatocytes was >460 min for all compounds.

Example 11

Plasma Protein Binding of Compounds of the Invention

The extent to which compounds of the invention bound to plasma proteins such as albumin and alpha-1 acid glycoprotein within human, rat or mouse plasma was determined by rapid equilibrium dialysis. Compounds were incubated at 5 µM for 4 hours at 37° C. Plasma protein binding for N,N-dimethyl-4-((6-oxopyrimidin-1(6H)-yl)methyl)benzamide in mouse plasma was 37.3%, in rat plasma was 14.8% and in human plasma was 30.6%.

Example 12

Activity of the Compounds of the Invention Against Cytochrome P450s

Using *E. coli* CYPEX membranes in combination with specific probe substrates, the inhibition of individual CYPs by compounds of the invention using the method described in Weaver et al., 2003, Drug Metab Dispos 31:7, 955-966 was assessed. Results are shown in Table 3.

TABLE 3

In vitro CYP inhibition data for N,N-dimethyl-4-
((6-oxopyrimidin-1(6H)-yl)methyl)benzamide

| CYP Inhibition (IC50 – µM) | | | | |
|---|---|---|---|---|
| 1A2 | 2C9 | 2C19 | 2D6 | 3A4 |
| >50 | >50 | >50 | >50 | >50 |

Example 13

Activity of Compounds of the Invention Against the HERG Channel

Compounds of the invention were tested for inhibition of cardiac potassium (hERG) channels using the Patchliner automated patch clamp. 6-Point concentration-response curves were generated using half-log serial dilutions from a maximum final test concentration of 100 µM. $IC_{50}$ values were obtained from a 4-parameter logistic fit of the concentration-response data. N,N-dimethyl-4-((6-oxopyrimidin-1(6H)-yl)methyl)benzamide was shown to have an IC50>100 µM with 7% inhibition at 100 µM. Reference compound values were consistent with those presented in the literature (Elkins et al., 2013 J. Pharm. Tox. Meth. 68:11-122).

Example 14

Activity of Compounds of the Invention Against a Panel of Enzymes, Ion Channels and Receptors Compounds of the invention were tested against the DiscoverX Safety47™ panel. N,N-dimethyl-4-((6-oxopyrimidin-1(6H)-yl)methyl)benzamide exhibited an exceptionally clean off target profile at 10 µM. No target was inhibited by more than 25% at this concentration.

Example 15

Aqueous Solubility of Compounds of the Invention

Compounds of the invention were shaken for 5 minutes with increasing amounts of water until a clear solution had formed. Using this method the solubility of N,N-dimethyl-4-((6-oxopyrimidin-1(6H)-yl)methyl)benzamide wass greater than 100 mg/ml.

Example 16

Activity of Compounds of the Invention in a Bacterial Reverse Mutation Test

The purpose of the bacterial reverse mutation test is to assess the mutagenic potential of the test item by its ability to revert the specified bacterial strains from auxotrophic growth to prototrophy. The assay detects point (gene) mutations at specific histidine or tryptophan loci, which may be induced by compounds that cause base pair substitutions or frameshift mutations in the genome of these organisms. Assays were performed in the presence and absence of an exogenous mammalian oxidative metabolising system (S-9 mix, a liver post-mitochondrial fraction derived from the livers of Aroclor 1254 treated rats), to mimic mammalian metabolism. The test methodology was based on established procedures for bacterial mutagenicity testing.

N,N-dimethyl-4-((6-oxopyrimidin-1(6H)-yl)methyl)benzamide was tested up to the guideline regulatory maximum dose level of 5000 µg/plate in all strains in the presence and absence of S-p9 mix.

There was no evidence of toxicity and no precipitation.

There were no increases in revertant numbers, greater than the defined fold-increases (to twice the relevant negative control value for TA98, TA100 or WP2 uvrA or three times the relevant negative control value for TA1535 or TA1537), in any strain at any dose level of N,N-dimethyl-4-((6-oxopyrimidin-1(6H)-yl)methyl)benzamide, in the presence or absence of S-9 mix, under plate incorporation conditions.

N,N-dimethyl-4-((6-oxopyrimidin-1(6H)-yl)methyl)benzamide was not mutagenic under the conditions of this test.

Example 17

Activity of Compounds of the Invention in an In Vitro Micronucleus Assay

The purpose of the in vitro micronucleus assay is to assess the ability of the test item to cause chromosome or spindle damage, or to interfere with the cell cycle, in ways which lead to the formation of micronuclei in the cytoplasm of TK6 cells. Chromosome defects are recognised as being the basis of a number of human genetic diseases. Micronuclei (MN) are the result of chromosome fragments or whole chromosomes remaining in the cytoplasm and not being incorporated into the nuclei of newly formed cells. These arise from damage to chromosomes leading to acentric fragments which cannot attach to the mitotic spindle; damage to the spindle apparatus preventing a chromosome from attaching to it or other interference with cell division. Assays were performed in the presence and absence of an exogenous mammalian oxidative metabolising system (S-9 mix, a liver post-mitochondrial fraction derived from the livers of Aroclor 1254 treated rats), to mimic mammalian metabolism. Cells were exposed to the test item for 3 hours and sampled 44 hours after the beginning of treatment. As a number of chemicals have been reported as only exerting positive effects following prolonged treatment, a continuous treatment of 27 hours in the absence of S-9 mix was also included. This was equivalent to 1.5 to 2.0 times the average generation time of cultured cells used in the assay. The test methodology was based on established procedures for in vitro micronucleus testing.

N,N-dimethyl-4-((6-oxopyrimidin-1(6H)-yl)methyl)benzamide was tested up to the regulatory maximum dose level of 1 mM (260 mg/mL) in all treatments. There was no precipitation and only slight cytotoxicity in the 27 hour treatment only. The relative increase in cell count (RICC) at 260 mg/mL was 105% in the presence of S-9 mix with 3 hour treatment, 98% in the absence of S-9 mix with 3 hour treatment and 74% in the absence of S-9 mix with 27 hour treatment, when compared with the concurrent negative control.

There were no statistically significant increases in percentage MN (% MN), either in the presence of S-9 mix with 3 hour treatment or in the absence of S-9 mix with 3 hour or 27 hour treatment. There was a significant trend in the absence of S-9 mix with 3 hour treatment, but as there were no statistically significant increases and all % MN counts were well within the 95% control limits of the HCD, this was considered to be not relevant.

N,N-dimethyl-4-((6-oxopyrimidin-1(6H)-yl)methyl)benzamide was neither clastogenic nor aneugenic in the presence or absence of S 9 mix, under the conditions of this test.

Example 18

Trypsin Inhibition by the Human Z A1AT Secreted in the Presence of Compounds of the Invention in the huZ Mouse The aim of the experiment was to purify human Z A1AT from three HuZ mice which had been treated with compound N,N-dimethyl-4-((6-oxopyrimidin-1(6H)-yl)methyl)benzamide (22.1e, 24.1a, 24.1b), then test the activity of the A1AT by reaction with increasing amounts of trypsin. Reaction of A1AT with the trypsin was analysed by western blot, probing with an anti-human A1AT antibody. A control plasma from a wild type mouse treated with the same compound (15.5b) was also included in the study.

Methods

Mice were treated with N,N-dimethyl-4-((6-oxopyrimidin-201(6H)-yl)methyl)benzamide at 200 mg/kg twice a day by oral gavage for 10 consecutive days. Mice had access to food (standard mouse chow, SAFE diets) and water ad libitum. On study day 10, each mouse was dosed 3.5-4.5 hours prior to terminal procedures. Blood was taken from each mouse by cardiac puncture and was collected into tubes containing EDTA 25 and plasma was prepared by centrifugation at 2700×g at 4° C. for 10 min. Plasma was aliquoted and stored at −80° C. prior to analysis.

100 µl of mouse plasma was diluted to 300 µl with 20 mM Tris, 150 mM NaCl, 5 mM EDTA, pH 7.4 (reaction and wash buffer) prior to purification. Washed α1-antitrypsin Select beads (150 µl) (GE Life Sciences) were then added to the plasma and mixed on a rocker for 30 minutes. The beads were then separated from the plasma by centrifugation using a spin column (Thermo Scientific). After washing the beads with 5×100 µl reaction buffer, the A1AT was then eluted from the beads with 3×100 µl 20 mM Tris, 150 mM NaCl, 0.6M $MgCl_2$, 5 mM EDTA, pH 7.4. The A1AT was eluted directly into 300 ul reaction buffer to ensure that the A1AT did not aggregate. Residual A1AT in the plasma and plasma supernatant was quantified using a human serpinA1 ELISA (Human Serpin A1/$\alpha_1$-antitrypsin duo set ELISA, R& D Systems, DY1268) to confirm depletion of human A1AT. The concentration of the eluted fractions were also measured. The amount of eluted A1AT was determined by measuring by A280 using an extinction coefficient of 0.45.

Figure 7A:
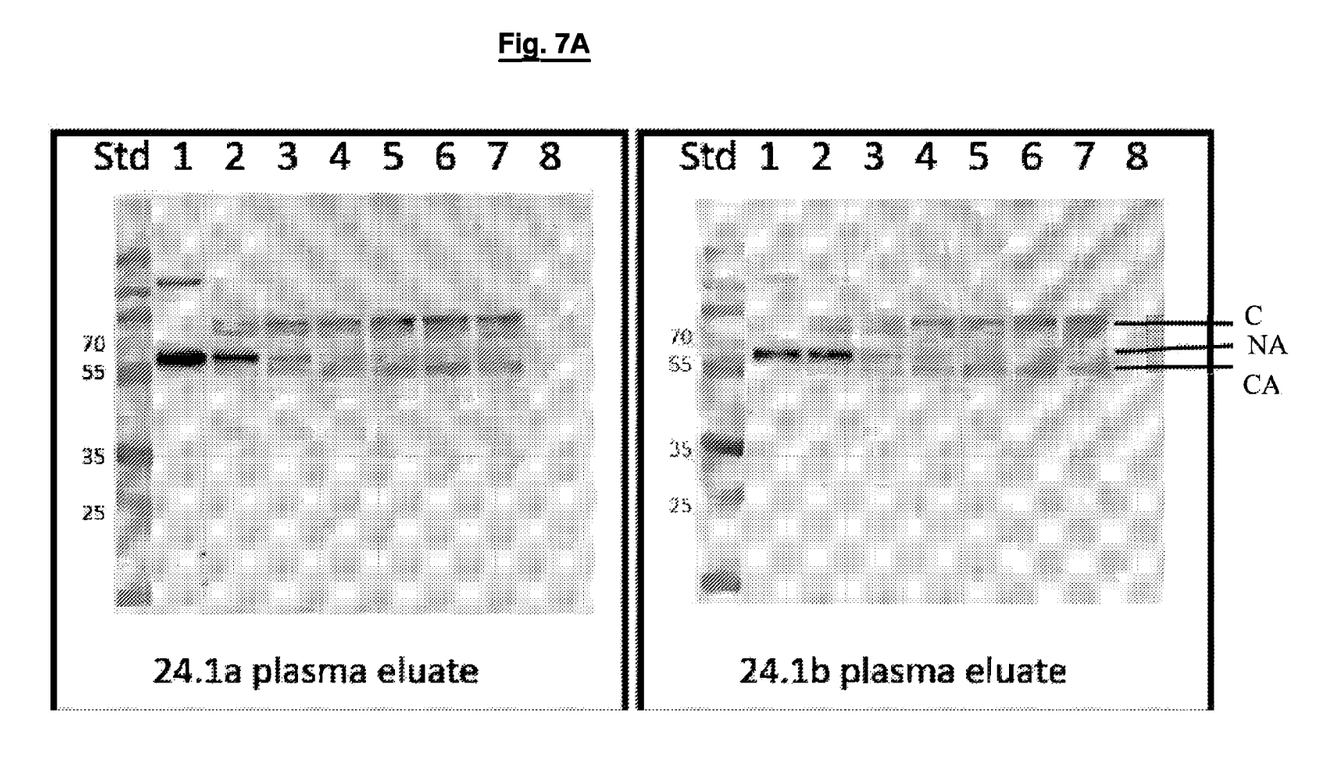
FIGS. 7A and B show Western blots of Z A1AT after isolation and treatment with trypsin. Z A1AT was isolated after treatment of one wild type (15.5b) and three HuZ mice (22.1e, 24.1a, 24.1b) with N,N-dimethyl-4-((6-oxopyrimidin-1(6H)-yl)methyl)benzamide at a dose level of 200 mgKg by oral gavage bid for 10 days. Each Western blot is labelled with the identifier of the mouse. Gel lanes are labelled according to Table 4. Protein bands are labelled as "C"—Complex, "NA"—Native antitrypsin, and "CA"—Cleaved antitrypsin.
Figure 7B:
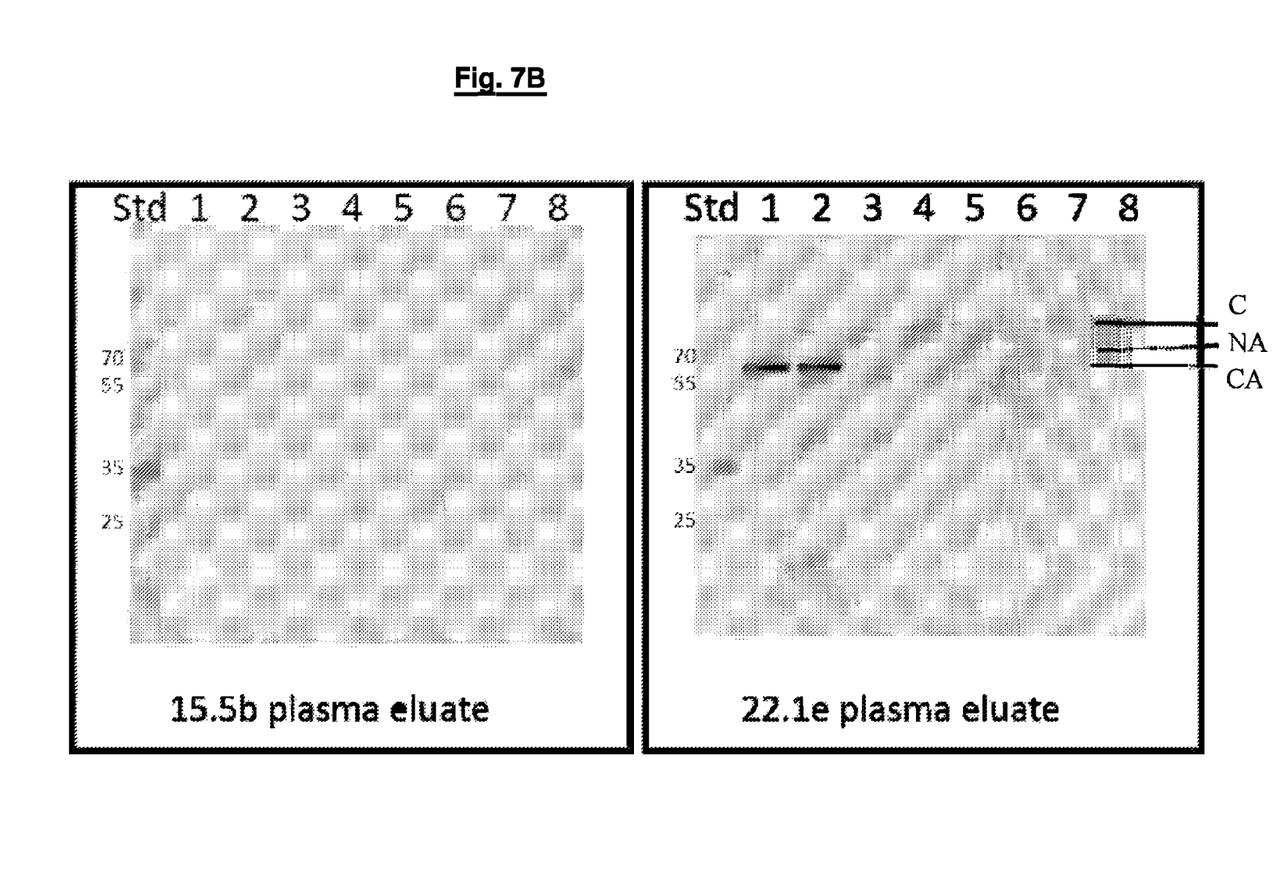

The activity of the eluted A1AT was tested by assessing its ability to form a complex with trypsin. Reaction mixtures were made up as in Table 4. Reactions were incubated for 5 minutes prior to the addition of 1 µl 1 mM 4-(2-aminoethyl) benzenesulfonyl fluoride hydrochloride. After a further 10 minutes 21 µl SDS sample buffer was added and boiled for 5 minutes. Samples were run on a 10% SDS gel and blotted onto nitrocellulose membrane. The membrane was then blocked with PBS 0.1% triton x-100, 5% skimmed milk powder, then probed with a rabbit anti human α-1 antitrypsin antibody (AbD serotec 0640-5039) overnight at 4° C. After washing the membrane with PBS, 0.1% triton X-100, 0.1% skimmed milk, the blots were probed with anti-rabbit IgG HRP conjugate. After further washes of the membrane the blots were developed using SuperSignal West pico PLUS chemiluminescent substrate (Thermo Scientific). The result is shown in FIGS. 7A and B.

TABLE 4

Experimental conditions for various treatments of isolated Z A1AT

| Gel lane | Approx. Molar Ratio (A1AT: trypsin) | A1AT (100 µg/ ml, 185 µM) | Trypsin (86 µg/ ml, 370 µM) | Buffer |
| --- | --- | --- | --- | --- |
| 1 | 1:0 | 10 µl | 0 µl | 10 µl |
| 2 | 4:1 | 10 µl | 1.25 µl | 8.75 µl |
| 3 | 2:1 | 10 µl | 2.5 µl | 7.5 µl |
| 4 | 1:1 | 10 µl | 5 µl | 5 µl |
| 5 | 1:1.25 | 10 µl | 6.25 µl | 3.75 µl |
| 6 | 1:1.5 | 10 µl | 7.5 µl | 2.5 µl |
| 7 | 1:2 | 10 µl | 10 µl | 0 µl |
| 8 | Trypsin Control | 0 µl | 5 ul | 15 µl |

Results

The data in FIGS. 7A and B show that no human A1AT could be detected in the plasma from the wild type control mouse (15.5b—see FIG. 7B). Human Z A1AT was detected in the three other samples from huZ mice (see FIGS. 7A and B). On reaction with increasing amounts of trypsin, all samples demonstrated complete reaction with trypsin as indicated by the loss of the native band (labelled "NA") and generation of complex ("C") or cleaved bands ("CA"), indicating that the Z A1AT in the eluted fraction is native and fully active.

The invention claimed is:

1. A compound represented by the structure of:

-continued

, or or a pharmaceutically acceptable salt of any one thereof.

2. The compound of claim 1, wherein the structure is represented by:

or pharmaceutically acceptable salt thereof.

3. The compound of claim 1, wherein the structure is represented by:

or pharmaceutically acceptable salt thereof.

4. The compound of claim 1, wherein the structure is represented by:

or pharmaceutically acceptable salt thereof.

5. A pharmaceutical composition comprising a compound or pharmaceutically acceptable salt of claim 1 and a pharmaceutically acceptable excipient.

6. A pharmaceutical composition comprising a compound or pharmaceutically acceptable salt of claim 2 and a pharmaceutically acceptable excipient.

7. A pharmaceutical composition comprising a compound or pharmaceutically acceptable salt of claim 3 and a pharmaceutically acceptable excipient.

8. A pharmaceutical composition comprising a compound or pharmaceutically acceptable salt of claim 4 and a pharmaceutically acceptable excipient.

* * * * *